United States Patent
Bonny

(10) Patent No.: US 6,960,648 B2
(45) Date of Patent: Nov. 1, 2005

(54) INTRACELLULAR DELIVERY OF BIOLOGICAL EFFECTORS

(75) Inventor: Christophe Bonny, Lausanne (CH)

(73) Assignee: Universite de Lausanne, Lausanne (CH)

( * ) Notice: Subject to any disclaimer, the term of this patent is extended or adjusted under 35 U.S.C. 154(b) by 232 days.

(21) Appl. No.: 09/977,831

(22) Filed: Oct. 15, 2001

(65) Prior Publication Data

US 2002/0120100 A1 Aug. 29, 2002

Related U.S. Application Data

(60) Provisional application No. 60/240,315, filed on Oct. 13, 2000.

(51) Int. Cl.$^7$ .......................... A61K 49/00; A61K 39/00; A61K 38/04
(52) U.S. Cl. ..................... 530/330; 435/325; 424/192.1; 424/193.1; 424/9.1
(58) Field of Search ...................... 435/6, 325, DIG. 35; 530/330; 424/192.1, 193.1, 9.1

(56) References Cited

U.S. PATENT DOCUMENTS 5,994,109 A * 11/1999 Woo et al. .................. 435/455
2003/0104622 A1 * 6/2003 Robbins et al. ............. 435/455

FOREIGN PATENT DOCUMENTS

| CA | 2094658 | | 4/1993 |
| FR | 2 767 323 | | 2/1999 |
| WO | WO 93/18759 | * | 9/1993 |
| WO | WO 94/23751 | | 10/1994 |
| WO | WO 98/51325 | | 11/1998 |
| WO | WO 98/51825 | | 11/1998 |
| WO | WO 99/07414 | | 2/1999 |
| WO | WO 00/12587 | | 3/2000 |
| WO | WO 01/64738 | | 9/2001 |
| WO | WO 02/31109 A2 | | 4/2002 |

OTHER PUBLICATIONS

Mauricio and Mandrup–Poulsen, Apoplosis and the Pathogenesis of IDDM: A Question of Life and Death, *Diabetes,* 47: 1537–1543 (1998).
Partial International Search Report for PCT/IB01/ 02423, Mailed on Jul. 2, 2002.
Anderson (1989). *Clin. Immun. and Immunopathol.* 53: S63–S71.
Ammendrup, et al. (2000). *Diabetes* 49: 1468–1476.
Bleich, et al. (1999). *J. Clin. Invest.* 103(10): 1431–1436.
Bonner–Weir (1994) *Recent Prog. Hormone Res.* 49: 91–104.
Bonny, et al. (2001). *Diabetes* 50: 77–82.
Breeman, et al. (1999). *Int. J. Cancer* 81: 658–665.
Brugidou, et al. (1995). *Biochem. Biophys. Res. Commun.* 214(2): 685–693.
Burns, et al. (1998) *J. Biol. Chem.* 273(20): 12203–12209.
Chen, et al. (2000). *Diabetes* 49: 562–570.
Dupraz, et al. (1999). *Gene Therapy* 8: 1160–1169.
Efrat, et al. (1988). *Proc. Natl. Acad. Sci. USA* 85: 9037–9041.
Flodstrom, et al. (1999). *Diabetes* 48: 706–713.
Giannoukakis, et al. (1999). *Diabetes* 48: 1730–1736.
Gibbs (2000). *Science* 287: 1969–1973.
Gibbs and Oliff (1994). *Cell* 79: 193–198.
Hofland, et al. (1999). *Proc. Assoc. Am. Physicians* 111(1): 63–69.
Ivanenkov, et al. (1999). *Biochem. Biophys. Acta* 1448: 463–472.
Ivanenkov, et al. (1999). *Biochem. Biophys. Acta* 1448: 450–462.
Cabibbo, et al. (1995). *Gene* 167: 41–47.
Iwahashi, et al. (1996). *Diabetologia* 30: 530–536.
Iwahashi, et al. (1998). *Cytokines, Cell. Mol. Ther.* 4: 45–51.
de Jong, et al. (1999). *J. Nucl. Med.* 40: 2081–2087.
Kato and Sugiyama (1997). *Critical Rev. Thera. Drug Carr. Systems* 14(3): 287–331.
Kim, et al. (2000). *Anticancer Res.* 20: 439–444.
Larsen, et al. (1998). *J. Biol. Chem.* 273(24): 15294–15300.
Lin, et al. (1995). *J. Biol. Chem.* 270(24): 14255–14258.
Lund, et al. (1990). *J. Biol. Chem.* 265(25): 15713–15723.
Mahato, et al. (1997). *Critical Rev. Thera. Drug Carr. Systems* 14(2): 133–172.
Mahato, et al. (1997). *J. Drug Targeting* 4(6): 337–357.
Mandrup–Poulsen (1996). *Diabetologia* 39: 1005–1029.
Mandrup–Poulsen (1998). *BMJ* 316: 1221–1225.
Mukherjee, et al. (1997). *Physiol. Rev.* 77(3): 759–803.
Negri, et al. (2000). *Genomics* 64: 324–330.
Nerup, et al. (1988). *Diabetes Care* 11(supp. 1): 16–23.
Oehlke, et al. (1998). *Biochem. Biophys. Acta* 1414: 127–139.
Offord, et al. (1997). *Meth. Enzymol.* 287: 348–369.
Pasqualini and Ruoslahti (1996). *Mol. Psychiatry* 1: 423.
Peralta, et al. (1990). *Endocrinol.* 127(2): 595–603.
Rabinovitch, et al. (1999). *Diabetes* 48: 1223–1229.
Renschler, et al. (1994). *Proc. Natl. Acad. Sci. USA* 91: 3623–3627.
Roitt (1991). *Essential Immunology.* Chapter 4: 65–83.
Rose and Vizzavona (1999) *J. Am. Chem. Soc. 121:* 7034–7038.
Rouquet et al. (1996). *Curr. Biol.* 6(9): 1192–1195.
Scharfmann and Czernichow (1996). *Diabetes and Metabolism* 22: 223–228.

(Continued)

Primary Examiner—Padmashri Ponnaluri
(74) Attorney, Agent, or Firm—Mintz, Levin, Cohn, Ferris, Glovsky and Popeo, P.C.; Ivor R. Elrifi

(57) ABSTRACT

The invention relates to a sequence of amino acids with the capacity to facilitate transport of an effector across a biological membrane. More specifically, the present invention relates to novel peptide transporters that specifically target certain cell types for the intracellular delivery of drugs and therapeutic agents.

4 Claims, No Drawings

OTHER PUBLICATIONS

Schwarze, et al. (1999). *Science 285*: 1569–1572.
Scott and Smith (1990). *Science 249*: 386–390.
Sjoholm (1995). *Call Death Diff. 5*: 461–468.
Smith and Jarrett (1988). *Laboratory Invest. 58*(6): 613–629.
Smith and Scott (1993). *Meth. Enzymol. 217*: 228–257.
Stephens, et al. (1997). *J. Autoimmunity 10*: 293–298.
Stephens, et al. (1999). *Endocrinol. 140*(7): 3219–3227.
Suzuki, et al. (2002). *J. Biol. Chem. 277*(4): 2437–2443.
Terskikh, et al. (1997). *Proc. Natl. Acad. Sci. USA 94*: 1663–1668.
Thorens (1992): *Proc. Natl. Acad. Sci. USA 89*: 8641–8645.
Torgerson, et al. (1998). *J. Immunology 161*: 6084–6092.
Ulbrich, et al. (2000). *J. Controlled Rel. 64*: 63–79.
Usami, et al. (1998). *Biochem Pharmacol. 55*: 185–191.
Wang, et al. (1990). *Endocrinol. 140*(3): 1200–1204.
Welsh, et al. (1999). *Mol. Med. 5*: 169–180.
Widmann, et al. (1995). *Biochem. J. 315*: 203–214.
Yamada, et al. (1999). *Diabetes 48*: 478–483.
Yoon, et al. (1999). *Science 284*: 1183–1187.
York, et al. (1999). *J. Biol Chem. 274*(2): 1164–1171.
Zacher, et al. (1980). *Gene 9*: 127–140.
Zeng, et al. (1996). *J. Peptide Sci. 2*: 66–72.
Zwick, et al. (1998). *Curr. Opin. Biotech. 9*: 427–436.
Pasquallini and Ruoslahti (1996). *Nature 380*: 364–366.
Sela and Zisman (1997). *FASEB J. 11*: 449–456.
Volz, et al. (1995). *FEBS Letters 373*: 23–29.
Yamato, et al. (1997). *Horm. Metab. Res. 29*: 56–59.
Bonny, et al. (2000), *J. Biol. Chem. 275*(22): 16466–16472.
Hoorens, et al. (1996). *J. Clin. Invest. 98*(7): 1568–1574.
Bonny, et al. (1998). *J. Biol. Chem. 273*(4): 1843–1846.
Gotoh, et al. (1987). *Transplantation 43*(5): 725–730.
Carithers and Lerner (1996) *Chem. Biol. 3*: 537–542.
Damke (1996). *FEBS Letters 389*: 48–51.
Hawiger (1999). *Current Opinion Chem. Biol. 3*: 89–94.
Avrameas, et al. (1998). *Proc. Natl. Acad. Sci. USA 95*: 5601–5606.
Rothbard, et al. (2000). *Nature Med. 6*(11): 1253–1257.
International Search Report for PCT/IB03/03097, mailed Sep. 30, 2004.

* cited by examiner

SEQUENCE LISTING

```
<160> NUMBER OF SEQ ID NOS: 37

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 1

Arg Arg Thr Lys
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 2

Arg Lys Leu Arg
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 3

Arg Arg Pro Lys
1

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: TRANSPORTER
```

```
            PEPTIDE

<400> SEQUENCE: 4

Pro Thr Ala Lys Pro Thr Tyr Thr Lys
  1               5

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 5

Ile Gln Gly Asn Gly Arg Gln Val Gly Cys Leu Thr Asn Lys
  1               5                  10

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 6

Met Arg Gly Leu Ser Lys Arg Gly
  1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 7

Arg Gln Phe Arg Lys
  1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 8

Arg Arg Ile Arg Gly
  1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 9

Asn Arg Arg Arg Gly Ile Asn
  1               5

<210> SEQ ID NO 10
```

```
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 10

Lys Gly Lys Trp
 1

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 11

Arg Gly Asn Arg Gly Ala Arg
 1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 12

Arg Arg Pro Arg
 1

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 13

Gly Arg Arg Lys Gly
 1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 14

Glu Arg Arg Lys
 1

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 15
```

```
Ser Gly Gly Arg Lys Gln Arg
1               5

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 16

Arg Ser Lys Arg
1

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 17

Arg Arg Ser Gly Arg
1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 18

Lys Gln Arg Arg
1

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 19

Gly Lys Arg Ala Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 20

Thr Gly Lys Arg Met Thr Arg
1               5

<210> SEQ ID NO 21
<211> LENGTH: 4
<212> TYPE: PRT
<213> ORGANISM: Artificial Sequence
<220> FEATURE:
```

```
<223> OTHER INFORMATION: Description of Artificial Sequence: TRANSPORTER
      PEPTIDE

<400> SEQUENCE: 21

Lys Arg Gly Arg
 1

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 22

Ser Leu Arg Arg Arg
 1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 23

Pro Ser Leu Arg Arg Pro Arg
 1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 24

Tyr Lys Arg Gly Arg
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 25

Gly Met Gly Arg Lys Pro Arg
 1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 26

Arg Arg Arg Val Gly
 1               5
```

```
<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 27

Arg Ser Phe Gly Val Lys Lys Tyr Gly
 1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 28

Lys Ser Leu Arg Ser Phe Lys
 1               5

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 29

Arg Val Arg Arg
 1

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 30

Pro Arg Ser Arg Arg
 1               5

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 31

Met Arg Arg Arg
 1

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 32
```

Tyr Gly Gly Lys Arg Thr Leu Ala Met Ser Lys
 1               5                  10

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 33

Gly Arg Arg Ser Arg
 1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: TRANSPORTER
      PEPTIDE

<400> SEQUENCE: 34

Tyr Pro Leu Pro Asn Met Lys
 1               5

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Caspase
      inhibitor peptide

<400> SEQUENCE: 35

Tyr Val Ala Asp
 1

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Inhibitor of
      NF-kB nuclear localization

<400> SEQUENCE: 36

Val Gln Arg Lys Arg Gln Lys Leu Met Pro
 1               5                  10

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: JNK Inhibitor

<400> SEQUENCE: 37

Arg Pro Lys Arg Pro Thr Thr Leu Asn Leu Phe Pro Gln Val Pro Arg
 1               5                  10                  15

Ser Gln Asp Thr
             20

INTRACELLULAR DELIVERY OF BIOLOGICAL EFFECTORS

RELATED APPLICATIONS

This application claims priority to U.S. Provisional Patent Application No. 60/240,315, filed on Oct. 13, 2000, which is incorporated herein by reference in its entirety.

TECHNICAL FIELD OF THE INVENTION

The invention relates to the field of molecular biology.

BACKGROUND OF THE INVENTION

Techniques enabling efficient transfer of a substance of interest from the external medium into cells, and particularly to cellular nuclei, are of considerable interest in the field of biotechnology. These techniques may be useful for protein or peptide production, for regulation of gene expression, for analysis of intracellular signaling channels and for the analysis of the effect of transport of a variety of different substances into a cell (or cell nucleus). One important application of such a technique is gene therapy. However, it is limited by the inability of the gene transfer vectors to transfer the biologically active substance into the cytoplasm or nuclei of cells in the host to be treated without affecting the host genome or altering the biological properties of the active substance.

Several techniques have been developed in an effort to efficiently transfer DNA into cells. Representative examples include coprecipitating DNA with calcium phosphate or DEAE-dextran or electroporation, both of which enable DNA to penetrate the plasma membrane and then enter the cell and/or nucleus. Both of these techniques suffer from low transfer efficiency and a high percentage of cell death. Other methods employ a conjugate of a virus-related substance with a strong affinity for DNA and a nucleic acid. However, the viral conjugates are difficult to use, and there are some risks related to the use of virus components. See, e.g., U.S. Pat. No. 5,521,291. Receptor-mediated endocytosis is also widely exploited in experimental systems for the targeted delivery of therapeutic agents into cells (36). Ligand-containing complexes are either selectively internalized by receptors located in the cell membrane which are specific for the ligands, or by specific antibodies located in membrane constituents. Endocytotic activity has been described for many receptors including IgG Fc, somatostatin, insulin, IGF-I and II, transferrin, EGF, GLP-1, VLDL or integrin receptors (35;37–43).

Proprotein convertases are also an example of a cell surface receptor which gets internalized through receptor mediated endocytosis. These proteins have been shown to be responsible for conversion of precursors of peptide hormones, neuropeptides, and many other proteins into their biologically active forms. All cleavage sites for the proprotein convertase family obey to the consensus R-X-X-R. The mammalian proprotein convertases can be classified into three groups on the basis of their tissue distribution. Furin, PACE4, PC5/PC6, and LPCIPC7/PC8/SPC7 are expressed in a broad range of tissues and cell lines. In contrast, expression of PC2 and PC1/PC3 is limited to neuroendocrine tissues, such as pancreatic islets, pituitary, adrenal medulla and many brain areas. Expression of PC4 is highly restricted to testicular spermatogenic cells. The neuroendocrine-specific convertases, PC2 and PC 1/PC3, are mainly localized in secretory granules. PC5/PC6A has also been reported to be localized to secretory granules. Furthermore, indirect evidence has suggested that a proportion of proprotein convertases molecules is present on the cell surface, and it has been shown that furin cycles between the TGN and the cell surface (reviewed in (1)). Taken together, these properties indicate that proprotein convertases transport extracellular ligands into the intracellular space.

The isolation of peptide sequences that direct efficient receptor-mediated endocytosis are profoundly boosted by the use of phage display technologies (44). Phage display libraries are extremely powerful tools that provide for a practically unlimited source of molecular variants including modifications of natural ligands to cell receptors (45) and short peptides (46). Similar libraries have also been injected directly into mice and peptide sequences that show a 13-fold selectivity for brain and kidney have been successfully isolated (48;49).

A need remains in the art for an efficient, non-biologically altering, low-risk means to target various cell types for the intracellular delivery of drugs and therapeutic agents. Thus, small transporter peptides that selectively target specific cell types may be derived from large phage display libraries. The advantages of small peptide carriers such as those obtained using phage display libraries include high quality and purity, low immunogenicity and the potential for highly efficient delivery to all cells in an organism (26). Accordingly, peptide carriers have the potential to improve upon conventional transporters such as liposomes or viruses for the efficient delivery of many macromolecules (see for example (50;51)).

SUMMARY OF THE INVENTION

The present invention provides transporter peptides which are capable of translocating across a biological membrane. The invention also relates to methods of using such transporter peptides to translocate an effector across a biological membrane.

In one aspect, the invention involves transporter peptides having at least one amino acid sequence selected from: $(X_m RX_o RX_n)$; $(X_m RRRX_n)$; $(X_m RRXRX_n)$; and $(X_m RXRRX_n)$, where X is a non-basic amino acid; m is an integer from zero to fourteen; n is an integer, independent of m, between zero and fourteen; o is an integer, independent of m and n, between zero and five; and wherein the transporter peptide is capable of translocating across a biological membrane.

In one embodiment, the invention provides a transporter peptide having the amino acid sequence R-X-X-R. In other embodiments, the invention provides a transporter peptide having an amino acid sequence of any one of SEQ ID NOS: 1–34. In various other embodiments, the transporter peptides are derived from protein convertase ligands. In still other embodiments, the transporter peptides are derived from protein convertase cleavage sites.

As used herein, a transporter peptide is a peptide that facilitates the translocation of a substance across a biological membrane.

In some embodiments, the transporter peptide is fused to an effector. The "effector" can be any suitable molecule, including DNA, RNA, a protein, a peptide, or a pharmaceutically active agent, such as, for example, a toxin, an antibiotic, an antipathogenic agent, an antigen, an antibody, an antibody fragment, an immunomodulator, an enzyme, or a therapeutic agent.

The term "fusion" or "fused" is meant to include all such specific interactions that result in two or more molecules showing a preference for one another relative to some third molecule. This includes processes such as covalent, ionic, hydrophobic, and hydrogen bonding, but does not include non-specific associations such as solvent preferences.

In various embodiments, the transporter peptide can be less than fifty (50), less than twenty-five (25), or less than fifteen (15) amino acids in length.

In further embodiments, translocation occurs within pancreatic B-cells, hepatocytes, colon cells, muscle cells and/or lung cells.

In another embodiment, the invention involves a method of translocating a transporter peptide across a biological membrane. For example, peptides of SEQ ID NOS: 1–6 can be translocated across a membrane of pancreatic B-cells; peptides of SEQ ID NOS: 7–10 can be translocated across a membrane of hepatocytes; the peptide of SEQ ID NO:11 can be translocated across a membrane of colon cells; peptides of SEQ ID NOS: 12–20 can be translocated across a membrane of muscle cells; and peptides of SEQ ID NOS: 21–34 can be translocated across a membrane of lung cells.

In yet another embodiment, the invention involves a transporter unit that is a transporter peptide conjugated to an effector. In various other embodiments, the effector may be a nucleic acid, a peptide, or a pharmaceutically active agent.

In still a further embodiment, the invention includes a method of producing a translocatable conjugate between a transporter peptide and an effector, forming a transporter peptide-effector conjugate. As used herein, "conjugate" or "conjugation" means any type of interaction enabling a physical association between an effector and a transporter peptide. The association may be covalent or a non-covalent in nature, and it must be sufficiently strong so that the vector does not disassociate before or during cellular penetration. Conjugation may be achieved using any chemical, biochemical, enzymatic or genetic coupling known to those skilled in the art. The effector of interest may be coupled to the N-terminal or C-terminal end of the transporter peptide.

In another embodiment, the invention includes a method of translocating an effector into the cytoplasm and nucleus of a eukaryotic cell, whereby the effector is conjugated to a transporter peptide and introduced into the eukaryotic cell. For example, the transporter peptide-effector conjugate can be introduced into the cell by incubating a cell culture in the presence of the conjugate or injecting the conjugate into the cell.

In various other embodiments, the invention includes a method of increasing the cellular concentration of an effector within a eukaryotic cell, whereby an effector is conjugated to a transporter peptide and incubated in a cell under conditions promoting active metabolism of the cell. A preferred embodiment of the invention includes use of a human cell as a eukaryotic cell.

In yet further embodiments, the invention includes a pharmaceutical composition containing a therapeutically or prophylactically effective amount of a transporter unit and a pharmaceutically acceptable carrier.

Preferred "pharmaceutical compositions" are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

In yet still further embodiments, the invention includes a kit in which one or more containers containing a therapeutically or prophylactically effective amount of a pharmaceutical composition.

Another embodiment of the invention involves a method of treating or preventing a disease by administering to a subject in which such treatment or prevention is desired, a pharmaceutical composition in an amount sufficient to treat or prevent a disease. For example, the disease to be treated may include diabetes, colon cancer, respiratory ailments, neurodegenerative disorders, cardioplegia and/or viral infections.

In another aspect, the invention involves a method of screening a phage library for transporter peptides, whereby a phage library is screened against specific cell types and it is then determined which cells have internalized phages.

In another embodiment, the invention includes identifying the DNA of an internalized phage and deducing an expressed peptide.

In yet a further embodiment, the invention includes a screening step whereby a phage library is panned for at least three cycles.

In still a further embodiment, the invention includes a phage having a multivalent display of peptides.

DETAILED DESCRIPTION OF THE INVENTION

The present invention provides a peptide transport system that specifically targets various cell types for the intracellular delivery of drugs and therapeutic agents. Existing transport systems in the art are too limited to be of general application because they are either inefficient, affect the host genome, alter the biological properties of the active substance, kill the target cell, or pose too high a risk to be used in a human subject due to the use of viral conjugates. The peptide transport system of the present invention uses proprotein convertases and specific ligands for the intracellular delivery of potential therapeutics, in order to overcome the limitations of transport systems in the art. The present system exhibits efficient delivery of an unaltered biologically active substance that does not affect the host's genome and that is otherwise non-invasive.

For example, transporter peptides have a use in treating diabetes. β-cell mass is tightly regulated so that insulin secretion maintains normoglycemia. Fitting β-cell mass to the needs of the infant or the adult organism, particularly in certain physiological and physiopathological conditions, is essentially attained by a dynamic balance between β-cell death and regeneration that occurs from differentiation of immature β-cells and from the proliferation of preexisting insulin-secreting cells (54;55). In Type I diabetes, impaired balance results from accelerated β-cell destruction, a process initiated by the specific attack of the immune system that targets pancreatic β-cells. Preventing or decreasing the rate of β-cell destruction may therefore not only help stabilize diabetes, but may also allow for islet regeneration to correct β-cell mass insuffisance.

Several molecules have been established as potent tools to decrease the rate of β-cell loss in experimental models of Type I diabetes. Many of these molecules are peptidyl in nature, and thus easily linked to peptide carriers. The peptides described herein serve as basis for the design of therapeutic "cargos", namely the coupling of the carriers ("transporter peptide") with therapeutic agents ("effectors").

Thus, a preferred embodiment of the transport system of the present invention targets β-cell intracellular mechanisms for the treatment of Type I diabetes. Type I diabetes is secondary to the destruction of the pancreatic β-cells by secretion of the immune system (1). Conclusive data, both in human and rodents, indicate that the cytokines interleukin-1β(IL-1β) in conjunction with TNFα and IFNγ, secreted by macrophages and T-cells, are major components responsible for the final outcome that leads to β-cell dysfunction and destruction and Type I diabetes (2–4). These secreted cytokines engage in a highly complex network of signaling and effector molecules in pancreatic β-cells. The signaling modifies the comportment of the cells and has a decisive impact on the cell fate. Accumulating evidence indicates that this regulatory intracellular network represents a promising target for the development of novel therapeutic approaches (5–11). Each of the molecules involved in the treatment and integration of intracellular cytokine signaling may represent a target for transporter-drug design.

Among the most prominent signaling molecules recruited by IL-1β in β-cells are ceramides, prostaglandins, heat-shock proteins, the inducible NO synthase enzyme (iNOS), the transcription factor NF-κB, and the three MAP kinases ERK1/2, p38 and JNK. Many of these molecules are targets for blockage with existing inhibitors that have led to improvement of β-cell survival and function. iNOS KO mice are resistant to IL-1β cytotoxicity (12) and blockers of iNOS activity prevent different aspects of NO cytotoxicity (reviewed in (6)). Islets and cell-lines studies have indicated that blockers of $Ca^{2+}$ channels or caspase inhibitors prevent rodent β-cell death (13;14). p38 inhibitors attenuate IL-1β-mediated inhibition of glucose-stimulated insulin release (15). β-cell specific suppression of GAD expression in antisense GAD transgenic NOD mice prevented autoinimune diabetes (16). Expression of bcl-2, IL-1Ra as do JBD (a dominant inhibitor of the c-Jun N-terminal Kinase JNK) in pancreatic β-cell lines had lead to the generation of cells that resist apoptosis (17–20). Together, these data indicate that the manipulation of intracellular events with specific tools holds great promise for the treatment of Type I diabetes.

One major challenge for disease treatment is to convert biologically important molecules into bioactive, cell-permeable compounds which are usable in vivo (21). For example, the most promising tools for the prevention of β-cell loss are a number of large proteins (e.g., Bcl-2 (8), inhibitors of cytokine signaling such as dominant negative versions of MyD88, TRAF, FADD or IRAK (22;23), or the JNK inhibitor $JBD_{280}$ (24)) that cannot be currently delivered in vivo to tissues and cell-types including pancreatic β-cells.

Recent work indicates progress in attempts to convert large proteins into small bioactive compounds which can be easily delivered to cells and organs (25). These techniques essentially require two conditions: 1) a specific transporter or a chemical modification thereof is linked to the molecules for efficient delivery inside cells (see, for example, efficient short peptide transporters described in (26–28)); and 2) the active portion of of the protein has to be narrowed down so that small peptides sequence might be linked to the transporter. In short, these conditions generally define 3–30 amino acid-long, bi-partite peptides that are able to enter cells while conserving the essential biological properties of the proteins from which they are derived. As in cancer research (32), there are numerous intracellular events in the β-cells whose manipulations protect β-cells from cytokine-induced apoptosis-manipulations which appear to be promising targets for drug design.

Receptor-mediated endocytosis is widely exploited in experimental systems for the targeted delivery of therapeutic agents into cells (36). Endocytotic activity is a common property that has been described for many receptors including IgG Fc, somatostatin, insulin, IGF-I and II, transferrin, EGF, GLP-1, VLDL or integrin receptors (35;37–43). Recently, the isolation of peptide sequences that direct efficient receptor-mediated endocytosis has been profoundly boosted by the use of phage display technologies (44). Phage display libraries are extremely powerful tools that provide for a practically unlimited source of molecule variants including modifications of natural ligands to cell receptors (45) and short peptides (46). Using this technology, evidence that cell-type specific receptors mediate endocytosis has been reported (47). Similar libraries have been injected directly into mice and peptide sequences that show a 13-fold selectivity for brain and kidney have been successfully isolated (48;49).

Although strong experimental background indicates that transporter peptides which selectively target pancreatic β-cells might be derived from large phage display libraries, no such attempts have been reported. The advantages of small peptide carriers such as those obtained using phage display libraries are numerous and include ease of generation by chemical synthesis, high quality and purity, low immunogenicity and potential for highly efficient delivery to all cells in an organism (26). Accordingly, the peptide carriers of the invention have the potential to perform better than more conventional transporters such as liposomes or viruses in the efficient delivery of many macromolecules (see for example (50;51)).

Phage peptide libraries are traditionally constructed in derivatives of the filamentous phage M13. Peptide libraries are fused to the minor coat protein III of the capsid that displays 1–5 copies of the peptide motif (46). Alternatively, high-valent display is attained by using the major coat protein pVIII.

These types of libraries have not been optimized for the isolation of receptor-mediated endocytotic peptide sequences, and the following considerations are relevant for the recovery of carriers with the highest efficiencies of internalization:

1) mono- or low-valent display of peptides is essentially insufficient for efficient uptake of such large structures as filamentous phages, however multivalent display allows for efficient uptake (44); and 2) the internalization of receptor-bound ligands involves concentration of cell surface receptors in specialized areas of the plasma membrane and subsequent formation of clathrin-coated vesicles (52).

The large size of the M13 derivatives (1–1.5 $\mu$m) (53) exceeds the typical size of classical clathrin-coated pits (150 nM). Clathrin-coated pits are invaginated structures on the plasma membrane that occupy approximately 2% of the membrane surface. These specialized structures direct the highly efficient receptor-mediated internalization process that clears extracellular proteins or peptides such as insulin or EGF at the extremely rapid rate of 10–50%/min (43). Thus, receptor-mediated internalization by these specialized and highly efficient structures is not expected to occur with the conventional M13 phages.

Accordingly, published attempts have failed to produce peptides that display a high internalization rate of peptide bearing phages. To date, no consensus internalization motif specific for a particular cell-type has emerged from these studies (44;47–49).

In certain aspects, the invention described herein relates to the identification of transporter peptides which promote the internalization of peptide-bearing phages. Once the peptide sequences are determined, that are bound to effector molecules in order to transport the effector molecules across a biological membrane.

As used herein, the terms "bound" or "binds" or "associates" or "interacts" are meant to include all specific interactions that result in two or more molecules showing a preference for one another relative to some third molecule. This includes processes such as covalent, ionic, hydrophobic, and hydrogen bonding, but does not include non-specific associations such as solvent preferences.

A transporter peptide is a peptide that facilitates the passage, or translocation, of a substance across a biological membrane, particularly into the cytoplasm or nucleus, of the cell. Translocation may be detected by various procedures, including a cellular penetration assay as described in, for example, PCT application No. WO 97/02840. Generally, a cellular penetration assay is performed by: a) incubating a cell culture with a translocating peptide; b) fixing and permeabilizing the cells; and c) detection of the presence of the peptides inside the cell. The detection step may be carried out by incubating the fixed, permeabilized cells with labeled antibodies directed to the peptide, followed by detection of an immunological reaction between the peptide and the labeled antibody. Alternatively, detection may also be achieved by using a detectably labeled peptide, and directly detecting the presence of the label in cellular compartments. The label may be, for example, a radioactive label, or a fluorescent label, or a dye.

The invention further includes transport units, which are complexes of the translocation peptide coupled to an effector. As used herein, "coupled" means any type of interaction enabling a physical association between an effector and the peptide. The association may be covalent or a non-covalent in nature, and it must be sufficiently strong so that the vector does not disassociate before or during translocation. Coupling may be achieved using any chemical, biochemical, enzymatic or genetic coupling known to those skilled in the art. The effector of interest may be coupled to the N-terminal or C-terminal end of the peptide vector.

An "effector" refers to any molecule or compound of, for example, biological, pharmaceutical, diagnosis, tracing, or food processing interest. It may consist of nucleic acids (ribonucleic acid, deoxyribonucleic acid) from various origins, and particularly of human, viral, animal, eukaryotic or prokaryotic, plant, synthetic origin, etc. A nucleic acid of interest may be of a variety of sizes, ranging from, for example, a simple trace nucleotide to a genome fragment, or an entire genome. It may a viral genome or a plasmid. Alternatively, the effector of interest may also be a protein, such as, for example, an enzyme, a hormone, a cytokine, an apolipoprotein, a growth factor, an antigen, or an antibody, etc. Furthermore, the effector may be a pharmaceutically active agent, such as, for example, a toxin, a therapeutic agent or an antipathogenic agent, such as an antibiotic, an antiviral, an antifungal, or an anti-parasitic agent. The effector of interest may itself be directly active or may be activated in situ by the peptide, by a distinct substance, or by environmental conditions.

The term "pharmaceutically active agent" is used herein to refer to a chemical material or compound which, when administered to an organism (human or animal) induces a detectable pharmacologic and/or physiologic effect.

The term "therapeutic agent" is used herein to refer to a chemical material or compound which, when administered to an organism (human or animal) induces a desired pharmacologic and/or physiologic effect.

The transporter peptides according to the present invention are characterized by the fact that their penetration capacity is virtually independent of the nature of the substance of the interest (the effector) that is coupled to it.

The invention also includes a method of introducing an substance of interest into a cell or a cell nucleus. The method includes contacting the cell with a transporter peptide-effector conjugate in an amount sufficient to enable efficient penetration into the cells. In general, the method may be used for in vivo or in vitro internalization of the conjugate. For example, the conjugate can be provided in vitro, ex vivo, or in vivo. Furthermore, it has been shown that a transporter peptide according to this invention is capable of potentializing the biological activity of the coupled substance. Therefore, another purpose of this invention is a method of using a transporter peptide that increases the biological activity of the effector to which it is coupled. According to the in vitro method, an effector is first coupled to a transporter, and the conjugate is incubated with cells at a temperature which enables active metabolism of the cells. In some cases, the transporter-effector conjugate is injected into particular cells. Those skilled in the art will recognize that any other method of introducing the conjugate into the cells can also be used.

In addition to the peptide-effector conjugates, the invention also provides a pharmaceutically acceptable base or acid addition salt, hydrate, ester, solvate, prodrug, metabolite, stereoisomer, or mixture thereof. The invention also includes pharmaceutical formulations comprising a peptide-effector conjugate in association with a pharmaceutically acceptable carrier, diluent, or excipient.

Salts encompassed within the term "pharmaceutically acceptable salts" refer to non-toxic salts of the compounds of this invention which are generally prepared by reacting the free base with a suitable organic or inorganic acid to produce "pharmaceutically-acceptable acid addition salts" of the compounds described herein. These compounds retain the biological effectiveness and properties of the free bases. Representative of such salts are the water-soluble and water-insoluble salts, such as the acetate, amsonate (4,4-diaminostilbene-2,2'-disulfonate), benzenesulfonate, benzonate, bicarbonate, bisulfate, bitartrate, borate, bromide, butyrate, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methylene-bis-2-hydroxy-3-naphthoate, embonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

According to the methods of the invention, a human patient can be treated with a pharmacologically effective amount of a peptide or conjugate. The term "pharmacologically effective amount" means that amount of a drug or pharmaceutical agent (the effector) that will elicit the biological or medical response of a tissue, system, animal or human that is being sought by a researcher or clinician.

The invention also includes pharmaceutical compositions suitable for introducing an effector of interest into a cell or cell nucleus. The compositions are preferably suitable for internal use and include an effective amount of a pharmacologically active compound of the invention, alone or in combination, with one or more pharmaceutically acceptable carriers. The compounds are especially useful in that they have very low, if any toxicity.

Preferred pharmaceutical compositions are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

Administration of the active compounds and salts described herein can be via any of the accepted modes of administration for therapeutic agents. These methods include systemic or local administration such as oral, nasal, parenteral, transdermal, subcutaneous, or topical administration modes.

Depending on the intended mode of administration, the compositions may be in solid, semi-solid or liquid dosage form, such as, for example, injectables, tablets, suppositories, pills, time-release capsules, powders, liquids, suspensions, or the like, preferably in unit dosages. The compositions will include an effective amount of active compound or the pharmaceutically acceptable salt thereof, and in addition, and may also include any conventional pharmaceutical excipients and other medicinal or pharmaceutical drugs or agents, carriers, adjuvants, diluents, etc., as are customarily used in the pharmaceutical sciences.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension.

If desired, the pharmaceutical composition to be administered may also contain minor amounts of non-toxic auxiliary substances such as wetting or emulsifying agents, pH buffering agents, and other substances such as for example, sodium acetate, triethanolamine oleate, etc.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

One approach for parenteral administration employs the implantation of a slow-release or sustained-released systems, which assures that a constant level of dosage is maintained, according to U.S. Pat. No. 3,710,795, incorporated herein by reference.

The compounds of the present invention can be administered in such oral dosage forms as tablets, capsules (each including timed release and sustained release formulations), pills, powders, granules, elixirs, tinctures, suspensions, syrups and emulsions. Likewise, they may also be administered in intravenous (both bolus and infusion) intraperitoneal, subcutaneous or intramuscular form, all using forms well known to those of ordinary skill in the pharmaceutical arts. An effective but non-toxic amount of the compound desired can be employed as an antiandrogenic agent.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, may be provided in the form of scored tablets containing 0.5, 1.0, 2.5, 5.0, 10.0, 15.0, 25.0, 50.0, 100.0, 250.0, 500.0 or 1000.0 mg of active ingredient.

Compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.1% to 15%, w/w or w/v.

The compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Any of the above pharmaceutical compositions may contain 0.1–99%, preferably 1–70% of the active compounds, especially compounds of the Formula I as active ingredients.

Equivalents. From the foregoing detailed description of the specific embodiments of the invention, it should be apparent that unique methods of translocation across a biological membrane have been described. Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims. For instance, the choice of the particular type of cell, or the particular effector to be translocated is believed to be a matter of routine for a person of ordinary skill in the art with knowledge of the embodiments described herein.

The details of one or more embodiments of the invention have been set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented in order to more fully illustrate the preferred embodiments of the invention. These EXAMPLES should in no way be construed as limiting the scope of the invention, as defined by the appended claims.

EXAMPLES

Example 1

Identification of Internalization Peptide Motifs

Included in this invention is a phage display library in a novel phage system that fulfills the following criteria: multivalent display of 4–50-mer peptides (>400 copies/phage); small size (50 nM); efficient recovery of internalized phages; removal of non-internalized bound-phages; and large number of individual peptide sequences ($3 \times 10^8$ independent clones, representing >$10^9$ heptapeptide sequences).

This library has been successfully used for the isolation of a peptide motif that directs efficient and specific intracellular delivery of macromolecules to the βTC-3 cell-model. In addition, this library has been used with five different (non-β-) cell lines, and in each case, the enrichment of peptide motifs specific for each cell-type has been observed. A general overview of the procedure is as follows:

Selection/enrichment Procedure

A phage display library is panned against a number of insulin-secreting cell-lines, rodent and human isolated islets and FACS purified β-cells, and finally is injected directly into animals (mice, rats, pigs) before extracting islets and recovering internalized phages. The panning procedure consists of at least three cycles of phage addition, recovery and amplification. Alternatively, and in order to isolate the most selective ligands, phages that bind other cell-types are subtracted by incubating the library with different non-insulin secreting cells before panning the library against β-cells. Experiments involving chloroquine to block lysosomal degradation are performed as described (44). These experiments are expected to produce different peptide carriers.

Determination of Phage Specificity

Panned phages are isolated and incubated with a number of different cells and organs. For example, in certain experiments, panned phages are incubated with insulin and non-insulin secreting cells and organs. Uptake is determined by counting the number of phages recovered. Immunocytochemistry studies are performed with anti-phage antibodies.

Characterization of Phage-beard Peptides

DNA from isolated phages are sequenced and expressed peptides are deduced. Peptides which direct internalization and mutated versions of these peptides are chemically synthesized and N-terminally labeled with FITC or iodinated. Labeled peptides are added to different cell types, isolated rodent and human islets, and directly injected into mice. Specificity of uptake, subcellular localization, clearance and stability are estimated (56).

Biochemical Assays

For analysis of insulin and non-insulin secreting cells, characterized peptides are linked to three known sequences: YVAD (caspases inhibitor (29), SEQ ID NO:35), VQRKRQKLMP (inhibitor of NF-κB nuclear localization (30), SEQ ID NO:36) or RPKRPTTLNLFPQVPRSQDT (JNK inhibitor (17), SEQ ID NO:37). These peptides are chemically synthesized and added to insulin and non-insulin secreting cells. Caspases, NF-κB and JNK are activated by the general activator etoposide (57) or anisomycin (58). Inhibition of caspases, NF-κB and JNK by the peptides are studied in β- and non β-cells. These experiments indicate whether the peptide carriers transport potential drugs in an active conformation specifically inside the β-cells.

Uptake of Potential Therapeutic Agents by the GLP-1 Receptor

Expression of the GLP-1 receptor (GLP-1R) is mainly restricted to the brain and the pancreas (66). The receptor is internalized following binding to an agonist (56). These properties make the GLP-1R an attractive tool to mediate preferential delivery of therapeutic agents to the pancreatic β-cells. This property is evaluated as described above. Information gathered with the GLP-1R assists, for example, in the design of bispecific dimers with enhanced selectivity.

Identification of Other Internalization Motifs for the GLP-1 Receptor

COS-7 cells transfected with the GLP-1R serve as substrates for a panning experiments as above. Newly identified motifs are evaluated for their specificity and their capacity to direct endocytosis.

Production of all-D-retro-inverso Peptides

In some embodiments, the peptides can be synthesized as retro-inverso peptides. All-D-retro-inverso peptides with increased stability and lower immunogenicity (59) are analyzed as described above.

Evolution has ensured the almost exclusive occurrence of L-amino acids in naturally occurring proteins. Virtually all proteases therefore cleave peptide bonds between adjacent L amino acids; thus, artificial proteins or peptides composed of D-amino acids are largely resistant to proteolytic breakdown. This resistance has been attractive to drug designers, but the exclusivity of biological systems for proteins made of L-amino acids means that such proteins cannot interact with the mirror image surface formed by enantiomeric proteins. Thus, an all D-amino acid protein usually has no biological effect or activity.

Linear modified retro-peptide structures have been studied for a long time (Goodman, 10 M., et al., On the Concept of Linear Modified Retro-Peptide Structures, Accounts of Chemical Research, 12(1), 1–7 (January, 1979)) and the term "retro-isomer" was designated to include an isomer in which the direction of the sequence is reversed compared with the parent peptide. By "retro-inverso isomer" is meant an isomer of a linear peptide in which the direction of the sequence is reversed and the chirality of each amino acid residue is inverted; thus, there can be no end-group complementarity.

More recently, Jameson et al. reportedly engineered an analogue of the hairpin loop of the CD4 receptor by combining these two properties: reverse synthesis and a change in chirality (Jameson et al., A rationally designed CD4 analogue inhibits experimental allergic. encephalomyelitis, Nature, 368, 744–746 (1994) and Brady, L. et al., Reflections on a Peptide, Nature, 368, 692–693 (1994)). The net result of combining D-enantiomers and reverse synthesis is that the positions of carbonyl and amino groups in each amide bond are exchanged, while the position of the side-chain groups at each alpha carbon is preserved. Jameson et al. reportedly demonstrated an increase in biological activity for their reverse D peptide, which contrasts to the limited activity in vivo of its conventional all-L enantiomer (owing to its susceptibility to proteolysis).

A partially modified retro-inverso pseudopeptide has been reported for use as a non-natural ligand for the human class I histocompatibility molecule, HLA-A2 (Guichard et al., Partially Modified Retro-Inverso Pseudopeptides as a Non-Natural Ligands for the Human Class I Histocompatibility Molecule HLA-A2, .1. Med. Chem. 39, 2030–2039 (1996)). The authors report that such non-natural ligands had increased stability and high MHC-binding capacity.

Retro-inverso peptides are prepared for peptides of known sequence in the following manner. A peptide having a known sequence (e.g., a tumor antigen peptide) is selected as a model peptide for designing and synthesizing a retro-inverso peptide analog. The analog is synthesized using D-amino acids by attaching the amino acids in a peptide chain such that the sequence of amino acids in the retro-inverso peptide analog is exactly opposite of that in the selected peptide which serves as the model. To illustrate, if the peptide model is a peptide formed of L-amino acids having the sequence ABC, the retro-inverso peptide analog formed of D-amino acids would have the sequence CBA. The procedures for synthesizing a chain of D-amino acids to form the retro-inverso peptides are known in the art and are illustrated in the above-noted references.

Since an inherent problem with native peptides is degradation by natural proteases, the peptides of the invention may be prepared to include the "retro-inverso isomer" of the desired peptide. Protecting the peptide from natural proteolysis should therefore increase the effectiveness of the specific heterobivalent or heteromultivalent compound.

A higher biological activity is predicted for the retro-inverso containing peptide when compared to the non-retro-inverso containing analog owing to protection from degradation by native proteinases.

Production of Modified Peptides

In some embodiments, the peptides can be synthesized as modified peptides. The modified peptides are be analyzed as described above.

Analogs can differ from the native peptides by amino acid sequence, or by modifications which do not affect the sequence, or by both. Preferred analogs include peptides whose sequences differ from the wild-type sequence (i.e., the sequence of the homologous portion of the naturally occurring peptide) only by conservative amino acid substitutions, preferably by only one, two, or three, substitutions, for example, substitution of one amino acid for another with similar characteristics (e.g., valine for glycine, arginine for lysine, etc.) or by one or more non-conservative amino acid substitutions, deletions, or insertions which do not abolish the peptide's biological activity.

Modifications (which do not normally alter primary sequence) include in vivo or in vitro chemical derivitization of peptides, e.g., acetylation or carboxylation. Also included are modifications of glycosylation, e.g., those made by modifying the glycosylation patterns of a peptide during its synthesis and processing or in further processing steps, e.g., by exposing the peptide to enzymes which affect glycosylation e.g., mammalian glycosylating or deglycosylating enzymes. Also included are sequences which have phosphorylated amino acid residues, e.g., phosphotyrosine, phosphoserine, or phosphothreonine.

The invention includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic will make the resulting peptide more stable and thus more useful as a therapeutic. Such mimetics, and methods of incorporating them into peptides, are well known in the art. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Blocking the charged amino- and carboxy-termini of the peptides would have the additional benefit of enhancing passage of the peptide through the hydrophobic cellular membrane and into the cell.

Production of Multivalent Peptides

Multivalent ligands display enhanced avidity of up to several orders of magnitude (60) that translates in enhanced rate of internalization (42). Monospecific dimers display great avidity and bispecific dimers are likely to have greater selectivity that may enhance their practical potential as specific cell-targeting agents (61). Multivalent peptides (both mono-and pluri-specific) are synthesized as peptidomimmetics, e.g., with either flexible peptidyl or sugar-based backbones (61–63).

Intracellular Localization

The different peptide sequences isolated may localize to different cell compartments (e.g., the nucleus, mitochondria, cytosol, etc.). This is carefully evaluated with iodinated and FITC-labeled peptides. This information is used for the design of the functional studies. For example, peptides accumulating in the cytosol are preferred for inhibiting NF-κB nuclear translocation, while peptides entering the nucleus are best suited for inhibiting JNK. In some embodiments, sequences such as nuclear localization motifs are added to redirect the carriers to the appropriate compartment.

Functional Studies

β-cell targeting peptides (e.g., L or D enantiomers, multivalent peptides) linked to the caspase, NF-κB or JNK inhibitors are added to β-cell lines, FACS purified β-cells and isolated human and rodent islets. Apoptosis is induced by IL-β (in conjunction with TNFα and IFNγ) and resistance to apoptosis is evaluated.

In vivo Experiments

NOD mice are injected in pre- and post-diabetic states with the effector peptides (β-cell targeting peptides linked to the caspase, NF-κB or JNK inhibitors). Dose and frequency of injection is determined as described above. Occurrence of diabetes is then measured.

Immunogenicity Assays

The immunogenic potential of the peptides is evaluated in rodents and rabbits.

Cloning

Peptide motifs that direct efficient uptake by specific cells are described in Example III. These peptides are used for the cloning and characterization of the cognate receptors from e.g., INS-1, βTC-3 and human islet cDNA libraries using established procedures (64;65).

Characterization

Tissue distribution of the cloned receptor(s) is evaluated by Northern and Western blotting of insulin and non-insulin secreting cells and organs. Binding kinetics, clearance and specificity of uptake are evaluated by transient transfection of the receptors in COS-7 cells. Control peptides are mutated sequences as well as known peptides such as, for example, GLP-1, GIP, glucagon, secretin, etc. Alternative internalization motifs for these receptors are characterized by panning the library in transfected COS-7 cells as described above.

Example II

Methods of Procedure for the Experiments

Phage Preparation and Enrichment Procedures

A library of $3 \times 10^8$ independent phages displaying random 15-mer epitopes at the surface of the capsids was generated using standard procedures (67). Phages were amplified then purified by polyethylene glycol (PEG) precipitation and finally resuspended at a concentration of $10^{10}$ infective particles per µl in Tris-EDTA buffer (10:1 mM, TE) as described (67). Phages ($10^{12}$) were added to cells in culture medium for 1 to 24 hours. Longer incubation times were preferred to favor isolation of phages that escaped proteolytic degradation in endocytotic vesicles. Following binding and internalization, cells were washed and non-internalized phages were destroyed by digestion with subtilisin (3 mg/ml) (44). Following extensive washing, internalized phages were then recovered by lysing cells in a buffer containing 2% deoxycholate, 10 mM Tris-HC1 and 2mM EDTA, pH 8.0. Recovered phages were finally amplified in *E. coli* cells (XL-1-Blue) and purified as described above. This preparation of selected phages was then used for a second round of panning. Three to five sequential rounds were performed to obtain enrichment of specific phage-bearing peptide sequences.

Immunocytochemistry and Fluorescence Studies

Single phages isolated according to the enrichment scheme above were amplified and added for 24 hours to cells in culture medium. Medium was then washed off and cells fixed in cold methanol-acetone (1:1) for 5 minutes. Antibodies directed against the phage capsid were used with a fluorescein-conjugated secondary antibody. Classical fluorescence microscopic studies and confocal microscopic assays were performed. Tissues were embedded in paraffin before processing.

Peptides

Peptides were synthesized using classical F-moc chemistry (Auspep, Australia), with a C-terminal amide group and labeled with FITC or iodinated when necessary. All peptides have been purified by HPLC and analyzed by Mass-Spectrometry.

Biochemical Studies

Peptides are added one hour before JNK, NF-κB and caspases will be activated in different cell-lines, such as, for example, βTC-3, INS-1 HeLa, WiDr, HepG2, NIH 3T3, COS-7, by etoposide (VP-16, Alexis) for 1 hour. Cell extracts are processed for JNK activity (using a solid phase JNK assay with c-Jun as substrate (68)), NF-κB nuclear translocation (electrophoretic mobility shift assay (30)) and caspase activity (using available commercial kits and antibodies, Upstate Biochemicals).

Measurement of Apoptosis

Apoptosis is measured using a combination of Hoechst 33342 and propidium iodide as previously described (68;69).

Islets

Islets are isolated by the method of Gotoh et al. (70). Human islets will be obtained from the "Insel Spital", Bern, Switzerland.

Mice

The exact dosage and time-frame of injection is optimized for each peptide. However, previous experience with JNKI peptides indicates that 100 μl of a 1 mM solution of peptides in PBS injected every two days is a reasonable starting point.

λZAP-Express Library

The INS-1 cDNA library in the λZAP-Express prokaryotic/eukaryotic expression vector has been used to clone the IB1 and IB2 cDNAs (71;72). This library is easily converted to a plasmid library under the control of the eukaryotic CMV promoter by simple helper phage excision (Stratagene).

Example III

Panning of Phase Display Library and Characterization of Internalized Peptide Motifs The ability of specifically targeting β-cells for drug delivery will have an enormous impact on the treatment of Type I diabetes. Blockers of β-cell destruction that essentially do not alter β-cell function (i.e. insulin secretion) already exist (e.g. JBD, bcl-2), and the conversion of one of these molecules (JBD) into a small peptide has been shown to retain full biological activity.

The pancreatic β-cell line βTC-3 was panned with the phage display library mentioned herein. Selective enrichment of the number of recovered phages was observed at each cycle of select ion as seen below in Table 1. Panning experiments using βTC-3 cells were performed with $10^9$ phages used at each step of the enrichment procedure. The number of phages recovered at 0° C. (no endocytosis) is less than 100, indicating that the background of extracellular, but not internalized, bound phages is extremely low under the conditions described herein.

TABLE 1

| Panning | Phages recovered |
| --- | --- |
| $1^{st}$ | $<1 \times 10^3$ |
| $2^{nd}$ | $2 \times 10^5$ |
| $3^{rd}$ | $3 \times 10^8$ |

The occurrence of phages recovered after three steps of panning in the βTC-3 cell line is seen in Table 2.

TABLE 2

| P1 | 61% |
| --- | --- |
| P6 | 17% |
| P8 | 5.5% |
| P10 | 5.5% |
| P65 | 5.5% |
| P66 | 5.5% |

Titration experiments were performed with the phage P1 (SEQ ID NO:1) incubated with βTC-3 cells for the times indicated in Table 3. The ratio of input/recovered phages is also shown. Titration experiments indicated that as much as 10% of the initial P1 phage input could be recovered.

TABLE 3

| Phage | Incubation | % Recovered |
| --- | --- | --- |
| P1 | 1 h | 0.01 |
|    | 5 h | 1 |
|    | 17 h | 10 |

Determination of the specificity of uptake was performed by titrating the number of recovered phages in 5 different cell lines. Phages ($10^8$) were incubated for 16 hours with the indicated cell lines, and the number of internalized and recovered phages was calculated as seen in Table 4. Control phages displaying an integrin internalization motif showed a similar number ($1-3 \times 10^6$) of recovered phages for all cell lines. This indicates that P1 (SEQ ID NO:1) is taken up by βTC-3 cells 10,000 to 1,000,000 fold more efficiently than by any other cell line tested.

TABLE 4

| Cells | Phages recovered |
| --- | --- |
| βTC-3 | $1 \times 10^7$ |
| HeLa | $<1 \times 10^2$ |
| WiDr | $2 \times 10^2$ |
| HepG2 | $<10$ |
| A549 | $10^3$ |

Peptides were then synthesized from the sequence of the displayed peptide in phage P1. The sequence of the P1 5-mer peptide was linked to a 10 amino-acid random sequence that was labeled with FITC. The control sequence was identical except that the P1 5-mer sequence was replaced by $(Ala)_5$. Peptides (10 μM) were added to the cells for one hour and cells were washed and fixed in cold methanol-acetone (1:1). FITC-labeled P1 peptides could be visualized inside βTC-3 cells, but not in other cell types.

Sequence analysis of 20 recovered phages at the final cycle of enrichment is shown in Table 5. Importantly, all sequences strictly obeyed to a same conserved consensus sequence of 5 amino acids. This suggests the specific selection/enrichment of a conserved motif that directs efficient uptake of the phages. A large proportion of the peptide motifs thus obtained obeys to the proprotein convertase consensus R-X-X-R. This observation forms the basis of the proposal to use proprotein convertases as vehicles for the intracellular delivery of potential drugs and macromolecules to specific cell-types.

TABLE 5

|  | Cell-Type | Sequence ID | Sequence | SEQ ID NO |
| --- | --- | --- | --- | --- |
| 1. | Pancreatic β-Cells | P1 | RRTK | 1 |
| 2. |  | P6 | RKLR | 2 |
| 3. |  | P66 | RRPK | 3 |
| 4. |  | I2 | PTAKPTYTK | 4 |
| 5. |  | I6 | IQGNGRQVGCLTNK | 5 |
| 6. |  | I10 | MRGLSKRG | 6 |
| 7. | Hepatocytes | H2 | RQFRK | 7 |
| 8. |  | H4 | RRIRG | 8 |
| 9. |  | H6 | NRRRGIN | 9 |
| 10. |  | H16 | KGKW | 10 |
| 11. | Colon Cancer | WP2 | RGNRGAR | 11 |
| 12. | Muscles | M1 | RRPR | 12 |
| 13. |  | M2 | GRRKG | 13 |
| 14. |  | M3 | ERRK | 14 |
| 15. |  | M4 | SGGRKQR | 15 |
| 16. |  | M6 | RSKR | 16 |
| 17. |  | M7 | RRSGR | 17 |
| 18. |  | M9 | KQRR | 18 |
| 19. |  | M11 | GKRAR | 19 |
| 20. |  | M13 | TGKRMTR | 20 |
| 21. | Lung | A2 | KRGR | 21 |
| 22. |  | A3 | SLRRR | 22 |
| 23. |  | A8 | PSLRRPR | 23 |
| 24. |  | A10 | YKRGR | 24 |
| 25. |  | A16 | GMGRKPR | 25 |
| 26. |  | T1 | RRRVG | 26 |
| 27. |  | T2 | RSFGVKKYG | 27 |
| 28. |  | T3 | KSLRSFK | 28 |

TABLE 5-continued

| Cell-Type | Sequence ID | Sequence | SEQ ID NO |
|---|---|---|---|
| 29. | T5 | RVRR | 29 |
| 30. | T7 | PRSRR | 30 |
| 31. | T8 | MRRR | 31 |
| 32. | T10 | YGGKRTLAMSK | 32 |
| 33. | T11 | GRRSR | 33 |
| 34. | T13 | YPLPNMK | 34 |

References

1. Mandrup-Poulsen, T. 1998. "Diabetes". BMJ. 316:1221.
2. Mandrup-Poulsen, T. 1996. "The role of interleukin-1 in the pathogenesis of IDDM". Diabetologia 39:1005.
3. Nerup, J., T. Mandrup-Poulsen, J. Molvig, S. Helqvist, L. Wogensen, and J. Egeberg. 1988. "Mechanisms of pancreatic beta-cell destruction in type I diabetes". Diabetes Care 11 Suppl 1:16.
4. Mauricio, D. and T. Mandrup-Poulsen. 1998. "Apoptosis and the pathogenesis of IDDM: a question of life and death". Diabetes 47:1537.
5. Iwahashi, H., N. Itoh, K. Yamagata, A. Imagawa, H. Nakajima, K. Tomita, M. Moriwaki, M. Waguri, K. Yamamoto, J. Miyagawa, M. Namba, T. Hanafusa, and Y. Matsuzawa. 1998."Molecular mechanisms of pancreatic beta-cell destruction in autoimmune diabetes: potential targets for preventive therapy". Cytokines. Cell Mol. Ther. 4:45.
6. Sjoholm, A. 1998. "Aspects of the involvement of interleukin-I and nitric oxide in the pathogenesis of insulin-dependent diabetes mellitus". Cell Death. Differ. 5:461.
7. Stephens, L. A., H. E. Thomas, and T. W. Kay. 1997." Protection of NIT-I pancreatic beta-cells from immune attack by inhibition of NF-kappaB". J. Autoimmun. 10:293.
8. Rabinovitch, A., W. Suarez-Pinzon, K. Strynadka, Q. Ju, D. Edelstein, M. Brownlee, G. S. Korbutt, and R. V. Rajotte. 1999. "Transfection of human pancreatic islets with an anti-apoptotic gene (bcl-2) protects beta-cells from cytokine-induced destruction". Diabetes 48:1223.
9. Bleich, D., S. Chen, B. Zipser, D. Sun, C. D. Funk, and J. L. Nadler. 1999. "Resistance to type I diabetes induction in 12-lipoxygenase knockout mice". J. Clin. Invest. 103:1431.
10. Welsh, M., L. Christmansson, T. Karlsson, S. Sandler, and N. Welsh. 1999. "Transgenic mice expressing Shb adaptor protein under the control of rat insulin promoter exhibit altered viability of pancreatic islet cells". Mol. Med. 5:169.
11. Chen, G., H. E. Hohmeier, R. Gasa, V. V. Tran, and C. B. Newgard. 2000. "Selection of insulinoma cell lines with resistance to interleukin-1beta- and gamma-interferon-induced cytotoxicity". Diabetes 49:562.
12. Flodstrom, M., B. Tyrberg, D. L. Eizirik, and S. Sandler. 1999. "Reduced sensitivity of inducible nitric oxide synthase-deficient mice to multiple low-dose streptozotocin-induced diabetes". Diabetes 48:706.
13. Wang, L., A. Bhattacharjee, Z. Zuo, F. Hu, R. E. Honkanen, P. O. Berggren, and M. Li. 1999. "A low voltage-activated Ca2+ current mediates cytokine-induced pancreatic beta-cell death". Endocrinology 140:1200.
14. Yamada, K., F. Ichikawa, S. Ishiyama-Shigemoto, X. Yuan, and K. Nonaka. 1999. "Essential role of caspase-3 in apoptosis of mouse beta-cells transf'ected with human Fas". Diabetes 48:478.
15. Larsen, C. M., K. A. Wadt, L. F. Juhl, H. U. Andersen, A. E. Karlsen, M.S. Su, K. Seedorf, L. Shapiro, C. A. Dinarello, and T. Mandrup-Poulsen. 1998. "Interleukin-1beta-induced rat pancreatic islet nitric oxide synthesis requires both the p38 and extracellular signal-regulated kinase ½ mitogen-activated protein kinases". J. Biol. Chem. 273:15294.
16. Yoon, J. W., C. S. Yoon, H. W. Lim, Q. Q. Huang, Y. Kang, K. H. Pyun, K. Hirasawa, R. S. Sherwin, and H. S. Jun. 1999. "Control of autoimmune diabetes in NOD mice by GAD expression or suppression in beta cells". Science 284:1183.
17. Bonny, C., A. Oberson, S. Negri, S. Stem, and D. F. Schorderet. 2000. "Cell-permeable peptide inhibitors of JNK with biological activity in mice". Diabetes 49: in Press.
18. Iwahashi, H., T. Hanafusa, Y. Eguchi, H. Nakajima, J. Miyagawa, N. Itoh, K. Tomita, M. Namba, M. Kuwajima, T. Noguchi, Y. Tsujimoto, and Y. Matsuzawa. 1996. "Cytokine-induced apoptotic cell death in a mouse pancreatic beta-cell line: inhibition by Bcl-2". Diabetologia 39:530.
19. Dupraz, P., C. Rinsch, W. F. Pralong, E. Rolland, R. Zufferey, D. Trono, and B. Thorens. 1999. "Lentivirus-mediated Bcl-2 expression in betaTC-tet cells improves resistance to hypoxia and cytokine-induced apoptosis while preserving in vitro and in vivo control of insulin secretion". Gene Ther. 6:1160.
20. Giannoukakis, N., W. A. Rudert, S. C. Ghivizzani, A. Gambotto, C. Ricordi, M. Trucco, and P. D. Robbins. 1999. "Adenoviral gene transfer of the interleukin-1 receptor antagonist protein to human islets prevents IL-ibeta-induced beta-cell impairment and activation of islet cell apoptosis in vitro". Diabetes 48:1730.
21. Gibbs, J. B. 2000."Mechanism-based target identification and drug discovery in cancer research". Science 287:1969.
22. Burns, K., F. Martinon, C. Esslinger, H. Pahl, P. Schneider, J. L. Bodmer, F. Di Marco, L. French, and J. Tschopp. 1998. "MyD88, an adapter protein involved in interleukin-1 signaling". J. Biol. Chem. 273:12203.
23. Stephens, L. A., H. E. Thomas, L. Ming, M. Grell, R. Darwiche, L. Volodin, and T. W. Kay. 1999. "Tumor necrosis factor-alpha-activated cell death pathways in NIT-I insulinoma cells and primary pancreatic beta cells". Endocrinology 140:3219.
24. Ammendrup, A., A. Oberson, K. Nielsen, N. Andersen, P. Serup, O. Madsen, T. Mandrup-Poulsen, and C. Bonny. 2000. "The c-Jun amino-terminal kinase pathway is preferentially activated by interleukin-1 and controls apoptosis in differentiating pancreatic β-cells". Diabetes 49: In Press.
25. Hawiger, J. 1999. "Noninvasive intracellular delivery of functional peptides and proteins". Curr. Opin. Chem. Biol. 3:89.
26. Schwarze, S. R., A. Ho, A. Vocero-Akbani, and S. F. Dowdy. 1999. "In Vivo Protein Transduction: Delivery of a Biologically Active Protein into the Mouse". Science 285:1573.
27. Brugidou, J., C. Legrand, J. Mery, and A. R.abie. 1995. "The retro-inverso form of a homeobox-derived short peptide is rapidly internalised by cultured neurones: a new basis for an efficient intracellular delivery system". Biochem. Biophys. Res. Commun. 214:685.
28. Oehlke, J., A. Scheller, B. Wiesner, E. Krause, M. Beyemiann, E. Klauschenz, M. Melzig, and M. Bienert.

28. 1998. "Cellular uptake of an alpha-helical amphipathic model peptide with the potential to deliver polar compounds into the cell interior non-endocytically". Biochim. Blophys. Acta 1414:127.
29. Rouquet, N., J. C. Pages, T. Molina, P. Briand, and V. Joulin. 1996. "ICE inhibitor YVADcmk is a potent therapeutic agent against in vivo liver apoptosis". Curr. Biol. 6:1192.
30. Lin, Y.-Z., S. Yao, R. A. Veach, T. R. Torgerson, and J. Hawiger. 1995. "Inhibition of nuclear translocation of transcription factor NF-κP by a synthetic peptide containing a cell membrane-permeable motif and nuclear localization sequence". J. Biol. Chem. 270:14255.
31. Torgerson, T. R., A. D. Colosia, J. P. Donahue, Y. Z. Lin, and J. Hawiger. 1998. "Regulation of NF-kappa B, AP-1, NFAT, and STAT1 nuclear import in T lymphocytes by noninvasive delivery of peptide carrying the nuclear localization sequence of NF-kappa B p50". J. Immunol. 161:6084.
32. Gibbs, J. B. and A. Oliff 1994. "Pharmaceutical research of molecular oncology". Cell 79.193.
33. de Jong, M., W. H. Bakker, B. F. Bernard, R. Valkema, D. J. Kwekkeboom, J.C. Reubi, A. Srinivasan, M. Schmidt, and E. P. Krenning. 1999. "Preclinical and initial clinical evaluation of 111In-labeled nonsulfated CCK8 analog: a peptide for CCK-B receptor-targeted scintigraphy and radionuclide therapy". J. Nucl. Med. 40:2081.
34. Breeman, W. A., L. J. Hofland, M. de Jong, B. F. Bernard, A. Srinivasan, D. J. Kwekkeboom, T. J. Visser, and E. P. Krenning. 1999. "Evaluation of radiolabelled bombesin analogues for receptor-targeted scintigraphy and radiotherapy". Int. J. Cancer 81:658.
35. Hofland, L. J., W. A. Breeman, E. P. Krenning, M. de Jong, M. Waaijers, P. M. van Koetsveld, H. R. Macke, and S. W. Lamberts. 1999. "Internalization of [I 251-Tyr3] Octreotide by somatostatin receptor-positive cells in vitro and in vivo: implications for somatostatin receptor-targeted radio-guided surgery". Proc. Assoc. Am. Physicians. 111:63.
36. Kato, Y. and Y. Sugiyama. 1997. "Targeted delivery of peptides, proteins, and genes by receptor-mediated endocytosis". Crit. Rev. Ther. Drug Carrier. Syst. 14:287.
37. Anderson, C. L. 1989. "Human IgG Fc receptors". Clin. Immunol. Immunopathol. 53:S63.
38. Lund, K. A., L. K. Opresko, C. Starbuck, B. J. Walsh, and H. S. Wiley. 1990. "Quantitative analysis of the endocytic system involved in hormone-induced receptor internalization". J. Biol. Chem. 265:15713.
39. Smith, R. M. and L. Jarett. 1988. "Receptor-mediated endocytosis and intracellular processing of insulin: ultrastructural and biochemical evidence for cell-specific heterogeneity and distinction from nonhormonal ligands". Lab. Invest. 58:613.
40. Soler, A. P., J. Alemany, R. M. Smith, F. de Pablo, and L. Jarett. 1990. "The state of differentiation of embryonic chicken lens cells determines insulin-like growth factor I internalization". Endocrinology 127:595.
41. Widmann, C., W. Dolci, and B. Thorens. 1995. "Agonist-induced internalization and recycling of the glucagon-like peptide-1 receptor in transfected fibroblasts and in insulinomas". Biochem. J. 310:203.
42. York, S. J., L. S. Arneson, W. T. Gregory., N. M. Dahms, and S. Kornfeld. 1999. "The rate of internalization of the mannose 6-phosphate/insulin-like growth factor H receptor is enhanced by multivalent ligand binding". J. Biol. Chem. 274:1164.
43. Mukherjee, S., R. N. Ghosh, and F. R. Maxfield. 1997. "Endocytosis". Physiol. Rev. 77:759.
44. Ivanenkov, V., F. Felici, and A. G. Menon. 1999. "Uptake and intracellular fate of phage display vectors in mammalian cells". Biochem. Biophys. Acta 1448:450.
45. Cabibbo, A., E. Sporeno, C. Toniatti, S. Altamura, R. Savino, G. Paonessa, and G. Ciliberto. 1995. "Monovalent phage display of human interleukin (hIL)-6: selection of superbinder variants from a complex molecular repertoire in the hIL-6 D-helix". Gene 167:41.
46. Zwick, M. B., J. Shen, and J. K. Scott. 1998. "Phage-displayed peptide libraries". Curr. Opin. Biotechnol. 9:427.
47. Ivanenkov, V. V., F. Felici, and A. G. Menon. 1999. "Targeted delivery of multivalent phage display vectors into mammalian cells". Biochem. Biophys. Acta 1448:463.
48. Pasqualini, it and E. Ruoslahti. 1996. "Organ targeting in vivo using phage display peptide libraries". Nature 380:364.
49. Pasqualuni, B. and B. Ruoslahti. 1996. "Tissue targeting with phage peptide libraries". Mol. Psychiatry 1:423.
50. Mahato, R. I., Y. Takakura, and M. Hashida. 1997. "Development of targeted delivery systems for nucleic acid drugs". J. Drug Target. 4:337.
51. Mahato, R. I., Y. Takakura, and M. Hashida. 1997. "Nonviral vectors for in vivo gene delivery: physicochemical and pharmacokinetic considerations". Crit. Rev. Ther. Drug Carrier. Syst. 14:133.
52. Damke, H. 1996. "Dynamin and receptor-mediated endocytosis". FEBS Lett. 389:48.
53. Zacher, A. N., C. A. Stock, J. W. Golden, and G. P. Smith. 1980. "A new filamentous phage cloning vector: fd-tet". Gene 9:127.
54. Scharfmann, R. and P. Czernichow. 1996. "Differentiation and growth of pancreatic beta cells". Diabetes Metab. 22:223.
55. Bonner-Weir, S. 1994. "Regulation of pancreatic beta-cell mass in vivo". Recent. Prog. Horm. Res. 49:91.
56. Widmann, C., W. Dolci, and B. Thorens. 1995. "Agonist-induced internalization and recycling of the glucagon-like peptide-1 receptor in transfected fibroblasts and in insulinomas". Biochem. J. 310:203.
57. Kim, R., Y. Ohi, H. Inoue, and T. Toge. 2000. "Enhancement of chemotherapeutic agents induced-apoptosis associated with activation of c-Jun N-terminal kinase I and caspase 3 (CPP32) in bax-transfected gastric cancer cells". Anticancer Res. 20:439.
58. Usami, I., M. Kubota, R. Bessho, A. Kátaoka, S. Koishi, K. Watanabe, M. Sawada, Y. W. Lin, Y. Akiyama, and K. Furusho. 1998. "Role of protein tyrosine phosphorylation in etoposide-induced apoptosis and NF-kappa B activation". Biochem. Pharmacol. 55:185.
59. Sela, M. and E. Zisman. 1997. "Different roles of D-amino acids in immune phenomena". FASEB J. 11:449.
60. Terskikh, A. V., J. M. Le Doussal, R. Crameri, I. Fisch, J. P. Mach, and A. V. Kajava. 1997. ""Peptabody": a new type of high avidity binding protein". Proc. Natl. Acad. Sci. U.S.A. 94:1663.
61. Carrithers, M. D. and M. R. Lerner. 1996. "Synthesis and characterization of bivalent peptide ligands targeted to G-protein-coupled receptors". Chem. Biol. 3:537.
62. Zeng, W., D. C. Jackson, and K. Rose. 1996. "Synthesis of a new template with a built-in adjuvant and its use in constructing peptide vaccine candidates through polyoxime chemistry". J. Pept. Sci. 2:66.
63. Ulbrich, K., V. Subr, I. Strohalm, D. Plocova, M. Jelinkova, and B. Rihova. "Polymeric drugs based on conjugates of synthetic and natural macromolecules. I. Synthesis and physico-chemical characterisation". J. Controlled Release.2000 Feb. 14.;64.(1.–3.):63.–79. 64:63.
64. Thorens, B. 1992. "Expression cloning of the pancreatic beta cell receptor for the gluco-incretin hormone glucagon-like peptide 1". Proc. Natl. Acad. Sci. U.S.A. 89:8641.
65. Volz, A., R. Goke, B. Lankat-Buttgereit, H. C. Fehmann, H. P. Bode, and B. Goke. 1995. "Molecular cloning, functional expression, and signal transduction of the GIP-receptor cloned from a human insulinoma". FEBS Lett. 373:23.
66. Yamato, E., H. Ikegami, K. Takekawa, T. Fujisawa, Y. Nakagawa, Y. Hamada, H. Ueda, and T. Ogihara. 1997. "Tissue-specific and glucose-dependent expression of receptor genes for glucagon and glucagon-like peptide-1 (GLP-1)". Horm. Metab. Res. 29:56.
67. Smith, G. P. and J. K. Scott. 1993. "Libraries of peptides and proteins displayed on filamentous phage". Methods Enzymol. 217:228.
68. Bonny, C., A. Oberson, M. Stelnm~nn, D. F. Schorderet, P. Nicod, and G. Waeber. 2000. "IB1 reduces cytokine-induced apoptosis of insulin-secreting cells". J. Biol. Chem. 275:16466.
69. Hoorens, A., M. Van de Casteele, G. Kloppel, and D. Pipeleers. 1996. "Glucose promotes survival of rat pancreatic beta cells by activating synthesis of proteins which suppress a constitutive apoptotic program". J. Clin. Invest. 98:1568.
70. Gotoh, M., T. Maki, S. Satomi, J. Porter, S. Bonner-Weir, C. J. O'Hara, and A. P. Monaco. 1987. "Reproducible high yield of rat islets by stationary in vitro digestion following pancreatic ductal or portal venous collagenase injection". Transplantation 43 :725.
71. Bonny, C., P. Nicod, and G. Waeber. 1998. "IB1, a JIP-I-related nuclear protein present in insulin-secreting cells". J. Biol. Chem. 273:1843.
72. Negri, S., A. Oberson, M. Steinmann P. Nicod, G. Waeber, D. F. Schorderet, and C. Bonny. 2000. "cDNA cloning and mapping of a novel islet-brain/JNK interacting protein". Genomics 64:324.

I claim:

1. A method of translocating a transporter peptide into a pancreatic B-cell, comprising contacting a pancreatic B-cell with a transporter peptide for a time and under conditions sufficient to allow a transporter peptide to translocate across a membrane of the B-cell, wherein the transporter peptide is SEQ ID NO:1.

2. The method of claim 1, wherein the transporter peptide contains one or more modified residues.

3. The method of claim 1, wherein the pancreatic B-cell is contacted in vivo.

4. The method of claim 1, wherein the pancreatic B-cell is contacted with a pharmaceutically acceptable salt of the transporter peptide.

* * * * *